United States Patent [19]

Ohsaka et al.

[11] Patent Number: 4,886,581

[45] Date of Patent: Dec. 12, 1989

[54] REMOVAL OF HYDROGEN FLUORIDE FROM 2,2,3,3-TETRA-FLUOROOXETANE

[75] Inventors: Yohnosuke Ohsaka; Shoji Takaki, both of Osaka; Hiroo Sakai, Takarazuka, all of Japan

[73] Assignee: Daikin Industries Ltd., Osaka, Japan

[21] Appl. No.: 68,935

[22] Filed: Jul. 1, 1987

[30] Foreign Application Priority Data

Jul. 3, 1986 [JP] Japan ................................. 61-157701

[51] Int. Cl.$^4$ ............................................. B01D 3/00
[52] U.S. Cl. ........................................ 203/80; 203/46; 203/67; 549/511
[58] Field of Search ....................... 203/71, 67, 73, 80, 203/46; 549/511

[56] References Cited

U.S. PATENT DOCUMENTS

| 4,031,110 | 6/1977 | Stockel et al. | 549/511 |
| 4,209,470 | 6/1980 | Lorquet | 260/653 |
| 4,226,777 | 10/1980 | Baum et al. | 549/511 |
| 4,496,760 | 1/1985 | Devic | 203/67 |
| 4,709,060 | 11/1987 | Ohsaka et al. | 549/511 |

FOREIGN PATENT DOCUMENTS

| 0645110 | 7/1962 | Canada | 203/67 |
| 0729160 | 3/1966 | Canada | 203/67 |
| 0098341 | 1/1984 | . | |
| 0150055 | 7/1985 | European Pat. Off. | 549/511 |
| 6197277 | 5/1986 | Japan . | |
| 1164471 | 9/1969 | United Kingdom | 549/511 |

Primary Examiner—Virginia Manoharan
Attorney, Agent, or Firm—Birch, Stewart, Kolasch & Birch

[57] ABSTRACT

By extracting hydrogen fluoride from 2,2,3,3-tetrafluorooxetane with a halogenated hydrocarbon, a mixture of 2,2,3,2-tetrafluorooxetane and the halogenated hydrocarbon containing a small amount of hydrogen fluoride is obtained. The mixture may be distilled at least twice to obtain a mixture of 2,2,3,2-tetrafluorooxetane and the halogenated hydrocarbon containing substantially no hydrogen fluoride.

4 Claims, No Drawings

REMOVAL OF HYDROGEN FLUORIDE FROM 2,2,3,3-TETRA-FLUOROOXETANE

BACKGROUND OF THE INVENTION

1. Field of the Invention

The present invention relates to a method for removing hydrogen fluoride from 2,2,3,3-tetrafluorooxetane (hereinafter referred to as "tetrafluorooxetane"). More particularly, it relates to a process for removing hydrogen fluoride from tetrafluorooxetane comprising extracting hydrogen fluoride from tetrafluorooxetane with a halogenated hydrocarbon and optionally at least twice distilling tetrafluorooxetane from which hydrogen fluoride is extracted with the halogenated hydrocarbon.

2. Description of the Prior Arts

Tetrafluorooxetane is useful as a solvent or a monomer for producing a straight chain polyether, and it is produced by reacting tetrafluoroethylene and paraformaldehyde in anhydrous hydrogen fluoride. However, separation of hydrogen fluoride from tetrafluorooxetane by distillation is difficult since boiling points of the former and the latter are 20° C. and 28° C., respectively. Conventionally, hydrogen fluoride is removed from tetrafluorooxetane by washing tetrafluorooxetane containing hydrogen fluoride with water. The washing method still has some problems such as neutralization and drying of washed tetrafluorooxetane and is not suitable for industrial application.

SUMMARY OF THE INVENTION

One object of the present invention is to provide a process for removing hydrogen fluoride from tetrafluorooxetane which does not require post-treatments such as neutralization and drying.

Another object of the present invention is to provide a process for removing hydrogen fluoride from tetrafluorooxetane suitable for industrial application.

These and other object of the present invention are achieved by a process for removing hydrogen fluoride from tetrafluorooxetane comprising extracting hydrogen fluoride from tetrafluorooxetane with a halogenated hydrocarbon to obtain a mixture of tetrafluorooxetane and the halogenated hydrocarbon containing a small amount of hydrogen fluoride, and optionally distilling said mixture to obtain a mixture of tetrafluorooxetane and the halogenated hydrocarbon containing a decreased amount of hydrogen fluoride and distilling the mixture of tetrafluorooxetane and the halogenated hydrocarbon to recover the mixture containing substantially no hydrogen fluoride.

DETAILED DESCRIPTION OF THE INVENTION

When tetrafluorooxetane produced by reacting tetrafluoroethylene and paraformaldehyde in hydrogen fluoride as described is directly distilled, an azeotropic mixture containing about 70% by weight of tetrafluorooxetane and about 30% by weight of hydrogen fluoride is obtained. When such azeotropic mixture is extracted with the halogenated hydrocarbon, a mixture of tetrafluorooxetane and the halogenated hydrocarbon containing a small amount, for example 0.1 to 1.0% by weight, preferably 0.2 to 0.5% by weight of hydrogen fluoride is obtained. Tetrafluorooxetane containing such small amount of hydrogen fluoride can be used for further reaction or in the final use without further purification.

Examples of the halogenated hydrocarbon used for the extraction of hydrogen fluoride from tetrafluorooxetane are trichloroethylene, tetrachloroethane, 1,1,1- or 1,1,2-trifluorotrichloroethane, 1,2-difluorotetrachloroethane, methylchloroform, tetrachloroethylene, p-chlorotoluene, p-chlorobenzotrifluoride and 3,4-dichlorobenzotrifluoride as well as mixtures thereof. Among them, 1,1,2-trichloro-1,2,2-trifluoroethane and 1,2-difluorotetrachloroethane are preferred.

According to the present invention, tetrafluorooxetane containing a small amount of hydrogen fluoride may be further purified by distillation. The distillation is carried out at least twice.

When 1,1,2-trichloro-1,2,2-trifluoroethane is used as the halogenated hydrocarbon, the first and second distillations may be carried out under following conditions:

First distillation
  Pressure: Atmospheric pressure to 5 kg/cm$^2$G, preferably to 2 kg/cm$^2$G
  Temperature of the bottom: 40° to 80° C.
Second distillation
  Pressure: Atmospheric pressure to 5 kg/cm$^2$G, preferable to 2 kg/cm$^2$G
  Temperature of the distillate: 30° to 70° C.

By the first distillation, a mixture of tetrafluorooxetane and the halogenated hydrocarbon containing less than 500 ppm, preferably 300 ppm of hydrogen fluoride is obtained as a bottom. Therefore, the bottom mixture obtained by the first distillation is further distilled to reduce the content of the halognated hydrocarbon in tetrafluorooxetane.

After the second distillation, an azeotropic mixture of the tetrafluooroxetane and the halogenated hydrocarbon containing substantially no hydrogen fluoride, namely less than 500 ppm of hydrogen fluoride is recovered. Since the halogenated hydrocarbon is a solvent, the mixture of tetrafluorooxetane and the halogenated hydrocarbon can be used for polymerization of tetrafluorooxetane to produce a straight chain polyether without further separation of them.

The present invention will be explained further in detail by following Examples.

EXAMPLE 1

An azeotropic mixture of 70% by weight of tetrafluorooxetane and 30% by weight of hydrogen fluoride being supplied at a rate of 20 l/hr. is extracted by circulating 1,1,2-trichloro-1,2,2-trifluoroethane in the mixture at a rate of 90 l/hr. at a temperature of 0° to 5° C. under pressure of 0.8 kg/cm$^2$G. to obtain a mixture of tetrafluorooxetane and 1,1,2-trichloro-1,2,2-trifluoroethane (weight ratio of 1:9) containing 0.2 to 0.5% by weight of hydrogen fluoride.

EXAMPLE 2

The mixture obtained in Example 1 was subjected to first distillation under following conditions:
Distillation Pressure: 0.8 kg/cm$^2$G
Supply amount of the mixture: 100 l/hr.
Temperature of the bottom: 56° C.
Outlet rate of the bottom: 97 l/hr.
Composition of the bottom:
  Hydrogen fluoride: 200 ppm
  Tetrafluorooxetane: 6 wt.%
  1,1,2-trichloro-1,2,2-trifluoroethane: 94 wt.%

Then, the bottom from the first distillation was again distilled under following conditions:

Distillation pressure: 0.8 kg/cm$^2$G
Rate of the mixture received from the still pot in first distillation: 97 l/hr.
Running temperature: 40° C.
Running rate: 10 l/hr.

By the second distillation, a mixture of tetrafluorooxetane and 1,1,2-trichloro-1,2,2-trifluoroethane of a weight ratio of 85:15 containing 100 to 500 ppm of hydrogen fluoride is obtained.

What is claimed is:

1. A process for removing hydrogen fluoride from 2,2,3,3-tetrafluorooxetane comprising extracting hydrogen fluoride from 2,2,3,3-tetrafluorooxetane with a halogenated hydrocarbon selected from the group consisting of trichloroethylene, tetrachloroethane, 1,1,1-trifluorotrichloroethane, 1,1,2-trifluorotrichloroethane, 1,2-difluorotetrachloroethane, methylchloroform, tetrachloroethylene, p-chlorotoluene, p-chlorobenzotrifluoride, 3,4-dichlorobenzotrifluoride and mixtures thereof to obtain a first mixture of 2,2,3,3-tetrafluorooxetane and the halogenated hydrocarbon containing 0.1 to 1.0% by weight of hydrogen fluoride; subjecting said first mixture to a first distillation at a temperature of 40°–80° C. and a pressure between atmospheric pressure and 5 kg/cm$^2$G to obtain a bottom mixture comprised of a second mixture of 2,2,3,3-tetrafluorooxetane and the halogenated hydrocarbon containing less than 500 ppm of hydrocarbon fluoride and subjecting said bottom mixture to a second distillation at a temperature of 30°–70° C. and a pressure between atmospheric pressure and 5 kg/cm$^2$G to recover an azeotropic mixture of 2,2,3,3-tetrafluorooxetane and the halogenated hydrocarbon containing substantially no hydrogen fluoride.

2. The process according to claim 1, wherein the halogenated hydrocarbon is 1,1,2-trifluorotrichloroethane or 1,2-difluorotetrachloroethane.

3. The process according to claim 2, wherein the halogenated hydrocarbon is 1,1,2-trifluorotrichloroethane.

4. The process according to claim 1, wherein the halogenated hydrocarbon of the obtained first mixture contains 0.2 to 0.5% by weight of hydrogen fluoride.

* * * * *